US006325825B1

(12) United States Patent
Kula et al.

(10) Patent No.: US 6,325,825 B1
(45) Date of Patent: Dec. 4, 2001

(54) STENT WITH VARIABLE WALL THICKNESS

(75) Inventors: John S. Kula, Stewartsville, NJ (US); James E. Umbach, Bethlehem, PA (US); Andreina Gomez, Tampa, FL (US)

(73) Assignee: Cordis Corporation, Miami Lakes, FL (US)

( * ) Notice: Subject to any disclaimer, the term of this patent is extended or adjusted under 35 U.S.C. 154(b) by 0 days.

(21) Appl. No.: 09/288,406

(22) Filed: Apr. 8, 1999

(51) Int. Cl.$^7$ ................................................ A61F 2/06
(52) U.S. Cl. .................................... 623/1.3; 623/1.15
(58) Field of Search .............................. 623/1.2, 1.15, 623/1.11, 1.3–1.31, 1.27, 1.17; 606/198, 194–195, 190, 200

(56) References Cited

U.S. PATENT DOCUMENTS

| | | |
|---|---|---|
| 3,657,744 | 4/1972 | Ersek ........................... 3/DIG. 1 |
| 4,503,569 | 3/1985 | Dotter ........................... 3/1.4 |
| 4,553,545 | 11/1985 | Maass et al. ................ 128/341 |
| 4,580,568 | 4/1986 | Gianturco .................... 128/345 |
| 4,681,110 | 7/1987 | Wiktor ......................... 128/343 |
| 4,733,665 | * 3/1988 | Palmaz ............................ 623/1 |
| 4,776,337 | 10/1988 | Palmaz ......................... 128/343 |
| 4,795,458 | 1/1989 | Regan ............................. 623/1 |
| 4,886,062 | 12/1989 | Wiktor ......................... 128/343 |
| 5,102,417 | 4/1992 | Palmaz ......................... 606/195 |
| 5,133,732 | 7/1992 | Wiktor ......................... 606/195 |
| 5,135,536 | 8/1992 | Hillstead ..................... 606/195 |
| 5,192,307 | 3/1993 | Wall ................................ 623/1 |
| 5,195,984 | 3/1993 | Schatz ......................... 606/195 |
| 5,266,073 | 11/1993 | Wall ................................ 623/1 |
| 5,269,802 | 12/1993 | Garber ......................... 606/191 |
| 5,290,305 | 3/1994 | Inoue ........................... 606/191 |
| 5,316,023 | 5/1994 | Palmaz et al. ............... 128/898 |
| 5,344,425 | 9/1994 | Sawyer ......................... 606/198 |
| 5,421,955 | 6/1995 | Lau et al. ....................... 216/48 |
| 5,443,498 | 8/1995 | Fontaine ......................... 623/1 |
| 5,443,500 | 8/1995 | Sigwart .......................... 623/1 |
| 5,496,365 | 3/1996 | Sgro ............................... 623/1 |
| 5,514,154 | 5/1996 | Lau et al. ..................... 606/195 |
| 5,527,354 | 6/1996 | Fontaine et al. ................ 623/1 |
| 5,569,295 | 10/1996 | Lam ............................. 606/198 |
| 5,591,197 | 1/1997 | Orth et al. ................... 606/198 |
| 5,603,721 | 2/1997 | Lau et al. ..................... 606/195 |
| 5,607,442 | 3/1997 | Fischell et al. .............. 606/191 |
| 5,643,312 | 7/1997 | Fischell et al. .............. 606/198 |
| 5,669,936 | 9/1997 | Lazarus .......................... 623/1 |
| 5,670,161 | * 9/1997 | Healy et al. .................... 604/8 |
| 5,733,303 | 3/1998 | Israel et al. ................. 606/198 |
| 5,776,161 | * 7/1998 | Globerman ...................... 623/1 |
| 5,807,404 | 9/1998 | Richter .......................... 623/1 |
| 5,836,964 | 11/1998 | Richter et al. ............... 606/194 |
| 5,836,966 | * 11/1998 | St. Germain ................. 606/198 |
| 5,931,867 | * 8/1999 | Haindl ............................ 623/1 |
| 6,013,854 | * 1/2000 | Moriuchi ........................ 623/1 |
| 6,027,526 | * 2/2000 | Limon et al. ................... 623/1 |

FOREIGN PATENT DOCUMENTS

| | | |
|---|---|---|
| 0 566 807 A1 | 10/1993 | (EP) ................. A61F/2/06 |
| 0 662 307 A1 | 7/1995 | (EP) ................. A61F/2/06 |
| 0 800 801 A1 | 10/1997 | (EP) ................. A61F/2/06 |
| 2 764 794 A1 | 12/1998 | (FR) ................. A61F/2/04 |
| WO 98/58600 | 12/1998 | (WO) .............. A61F/2/06 |

* cited by examiner

*Primary Examiner*—Cary E. O'Connor
(74) *Attorney, Agent, or Firm*—Paul A. Coletti

(57) ABSTRACT

A stent is made flexible along its length. The stent initially starts as a metal sheet. It is rolled in its central region to a specified wall thickness. Thereafter, the stent is photochemically etched to produce the desired cell pattern of the design of the stent. Then, the stent is folded and the metal is joined to give rise to a stent with multiple wall thickness. For instance, larger wall thicknesses at the end of the stent versus smaller wall thicknesses at its center. Various other possible manufacturing methods are useful with respect to this stent.

14 Claims, 12 Drawing Sheets

STENT WITH VARIABLE WALL THICKNESS

FIELD OF THE INVENTION

This invention relates to stents. In general, this invention relates to stents made more flexible, based on their overall structure; specifically, this invention relates to varying the wall thickness of a stent in order to create a more flexible stent; and also to improve radioopacity of the stent while not effecting its flexibility.

BACKGROUND OF THE INVENTION

A stent is commonly used as a tubular structure left inside the lumen of a vessel or duct of the body, in order to relieve an obstruction in the lumen or duct. Commonly, stents are inserted into the lumen in their unexpanded form; the stents are then expanded on their own (or with the aid of a second device) in situ at the obstruction. A typical method of expansion occurs through the use of a catheter-mounted stent on an angioplasty balloon, which balloon is inflated within the stenosed vessel or body passageway. This inflation causes the obstructions of the vessel associated with the wall components of the vessel to compress. Thereafter, the stent holds the obstruction in place at the vessel wall, and an enlarged lumen is obtained.

It is fairly commonly believed that usage of a stents is a technology transforming the type of therapy used against stenosis of a lumen. That is, in the absence of a using a stent, (in other words, when a balloon used alone) restenosis often occurs, as a result of elastic recoil of the stenotic lesion away from the vessel wall. So, stents have been hailed as a breakthrough in the use of science to improve medicinal therapies.

Although a number of stent designs have been created, the designs of these stents have exhibited a number of limitations, such as a general restriction on the dimension of the stent. For instance, typical stents have been limited to a pair of generally rigid ends (approx. 8 mm) and a flexible middle section (anywhere from about 7 mm to about 21 mm). This device is formed of multiple parts and is not continuously flexible along the longitudinal axis. Other stent designs with rigid segments and flexible segments have also been described.

Other stents are described as longitudinally flexible, but consist of a plurality of cylindrical elements connected by flexible members. This design has at least one important disadvantage, for example, according to this design, protruding edges occur when the stent is flexed around a curve raising the possibility of inadvertent retention of the stent on plaque deposited on arterial walls. This may cause the stent to embolize or more out of position and further cause damage to the interior lining of healthy vessels. Thus, balloon expandable stents known in the art, generally compromise axial flexibility to permit expansion and provide overall structural integrity.

However, it is further more desirable to be able to vary the flexibility of the stent along its length. In other words, it may be more desirable to have a stiffer stent at the proximal end and a more flexible stent at the distal end, or vice versa. To be able to vary the flexibility of the stent along its length could provide for emplacement of the proximal end in a narrower or more tortuous coronary artery, while stabilizing the stent at its proximal end. Or, it might be desirable to vary the flexibility in the center of the stent in order to achieve a bend of a particular coronary artery. If the stent could be produced reliably and quickly, it may be possible to examine the patient, determine the degree of tortuosity of the patient's coronary arteries, and then construct the stent to tailor to the patient.

SUMMARY OF THE INVENTION

The present invention overcomes some perceived shortcomings of prior art stents by providing a stent with axial flexibility. In a preferred embodiment, the stent has a first end and a second end with an intermediate section between the two ends. The stent further has a longitudinal axis and comprises a plurality of longitudinally disposed bands, wherein each band defines a generally continuous wave along a line segment parallel to the longitudinal axis. A plurality of links maintains the bands in a tubular structure. In a further embodiment of the invention, each longitudinally disposed band of the stent is connected, at a plurality of periodic locations, by a short circumferential link to an adjacent band. The wave associated with each of the bands has approximately the same fundamental spatial frequency in the intermediate section, and the bands are so disposed that the waves associated with them are spatially aligned so as to be generally in phase with one another. The spatially aligned bands are connected, at a plurality of periodic locations, by a short circumferential link to an adjacent band. In particular, at each one of a first group of common axial positions, there is a circumferential link between each of a first set of adjacent pairs of bands.

At each one of a second group of common axial positions, there is a circumferential link between each of a second set of adjacent rows of bands. Thus along the longitudinal axis, a common axial position occurs alternately in the first group and in the second group of axial positions. Then, the first and second sets are selected so that a given band is linked to a neighboring band at only one of the first and second groups of common axial positions.

In a preferred embodiment of the invention, the spatial frequency of the wave associated with each of the bands is decreased in a first end region lying proximate to the first end and in a second end region lying proximate to the second end. By comparison this will make the ends of the stent "stiffer." In a further embodiment of the invention, the spatial frequency of the bands in the first and second end regions is decreased by 20% compared with the spatial frequency of the bands in the intermediate section. The first end region may be located between the first end and a set of circumferential links lying closest to the first end and the second end region lies between the second end and a set of circumferential links lying closest to the second end. The widths of corresponding sections of the bands in these end regions, measured in a circumferential direction, are greater in the first and second end regions than in the intermediate section. Each band includes a terminus at each of the first and second ends and the adjacent pairs of bands are joined at their termini to form a closed loop.

In a further embodiment of the invention, a stent is provided that has first and second ends with an intermediate section between the two. This stent has further increased axial flexibility. This stent includes a plurality of longitudinally disposed bands, wherein each band defines a generally continuous wave having a spatial frequency along a line segment parallel to the longitudinal axis, the spatial frequency of the wave associated with each of the bands being decreased in a first end region lying proximate to the first end and in a second end region lying proximate to the second end, in comparison to the spatial frequency of the wave in the intermediate section; and a plurality of links for maintaining the bands in a tubular structure. The first and second regions have been further defined as the region that lies between the first and second ends and a set of circumferential links lying closest to the first end and second end. In a further embodiment the widths of the sectionals of the bands, measured in a circumferential direction, are greater in the first and second end regions than in the intermediate section.

In yet an additional embodiment, the stent is divided into a group of segments. Each of the segments are connected by a flexible connector. In addition, the stent segments are provided with enhanced flexibility at the flexible connectors, due to the geometrical configuration of the flexible connectors.

Furthermore the objects of the invention are accomplished with the stent being made flexible along its length. The stent initially starts as a metal sheet. It is rolled in its central region to a specified wall thickness. Thereafter, the stent is photochemically etched to produce the desired cell pattern of the design of the stent. Then, the stent is folded and the metal is joined to give rise to a stent with multiple wall thickness. For instance, larger wall thicknesses at the end of the stent versus smaller wall thicknesses at its center. Various other possible manufacturing methods are certainly perceived to be possible with respect to this stent. Alternately, the stent can be etched in its tubular configuration with the same desired effect.

These and other objects of the present invention will be better understood with reference to the attached figures and Detailed Description of the Invention which follow.

DETAILED DESCRIPTION OF THE DRAWINGS

The foregoing aspects of the invention will be more readily understood by reference to the following detailed description, taken with the accompanying drawings, in which:

FIGS. 1(a) and 1(b) are side views of a stent having circumferentially disposed bands wherein the stent is in axially unbent and bent positions respectively, the latter showing protruding edges;

FIGS. 1(c) and 1(d) are side views of an axially flexible stent in accordance with the present invention wherein the stent is in unbent and bent positions respectively, the latter displaying an absence of protruding edges;

FIG. 2 is a side view of a portion of the stent of FIGS. 1(c) and 1(d) showing the longitudinal bands, spaces, and inner radial measurements of bends in the bands being measured in inches;

FIGS. 3(a) and 3(b) show a portion of the stent of FIG. 2 with two bands between two circumferential links (a) before expansion in the undeformed state; and (b) after expansion, in the deformed state;

DESCRIPTION OF THE INVENTION

Improvements afforded by embodiments of the present invention include the following. First, there is an increased flexibility in two planes of the non-expanded stent while maintaining radial strength and a high percentage open area after expansion. Second, the stent of this invention provides even pressure on the expanding stent that ensures the consistent and continuous contact of expanded stent against artery wall. Third, the stent affords an avoidance of protruding parts during bending. Fourth, there is a removal of existing restrictions on maximum of stent. Fifth, the stent reduces any shortening effect during expansion of the stent.

In a preferred embodiment of the invention, an expandable cylindrical stent 10 is provided having a fenestrated structure for placement in a blood vessel, duct or lumen to hold the vessel, duct or lumen open, more particularly for protecting a segment of artery from restenosis after angioplasty. The stent 10 may be expanded circumferentially and maintained in an expanded, circumferentially rigid configuration. The stent 10 is axially flexible and when flexed at a band, the stent 10 avoids any externally protruding component parts.

FIG. 1 shows what happens to a stent 10, of a similar design to a preferred embodiment herein but utilizing instead a series of circumferentially disposed bands, when caused to bend in a manner that is likely encountered within a lumen of the body. A stent 10 with a circumferential arrangement of bands (1) experiences an effect analogous to a series of railroad cars on a track. As the row of railroad cars proceeds around the bend, the corner of each car proceeding around the bend after the coupling is caused to protrude from the contour of the track. Similarly, the serpentine circumferential bands have a series of protrusions (2) above the surface of the stent 10 as the stent 10 bends.

Figure 1A:
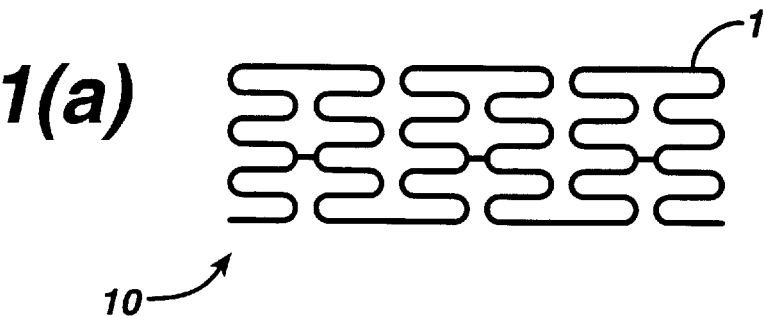
Figure 1B:
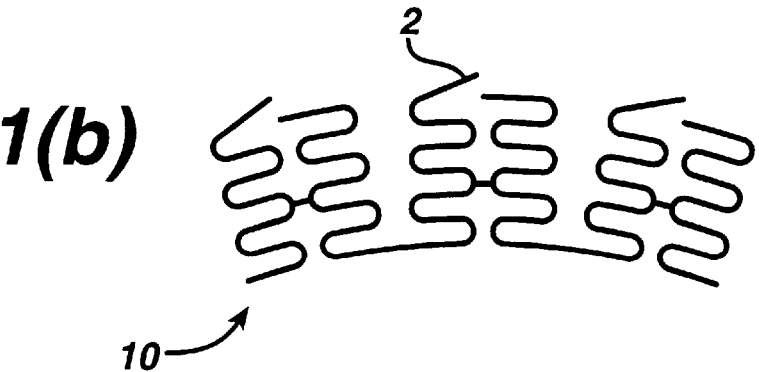
Figure 1C:
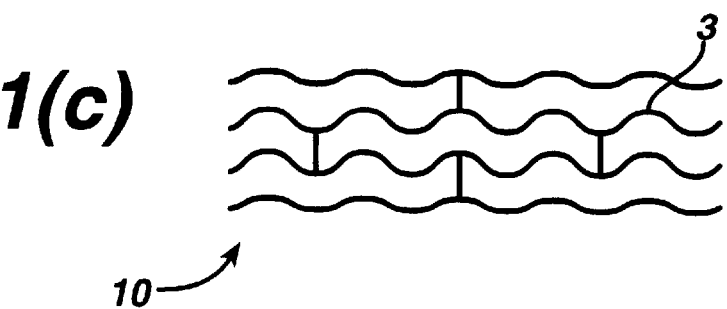
Figure 1D:
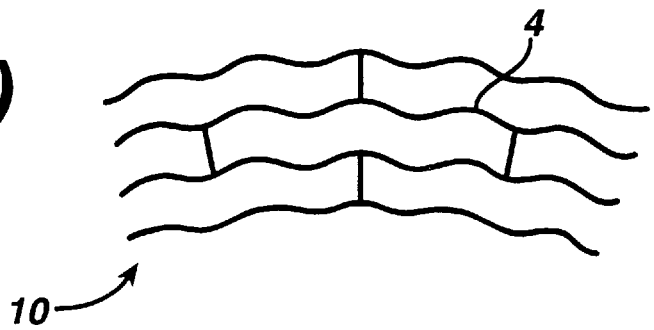
Figure 7:
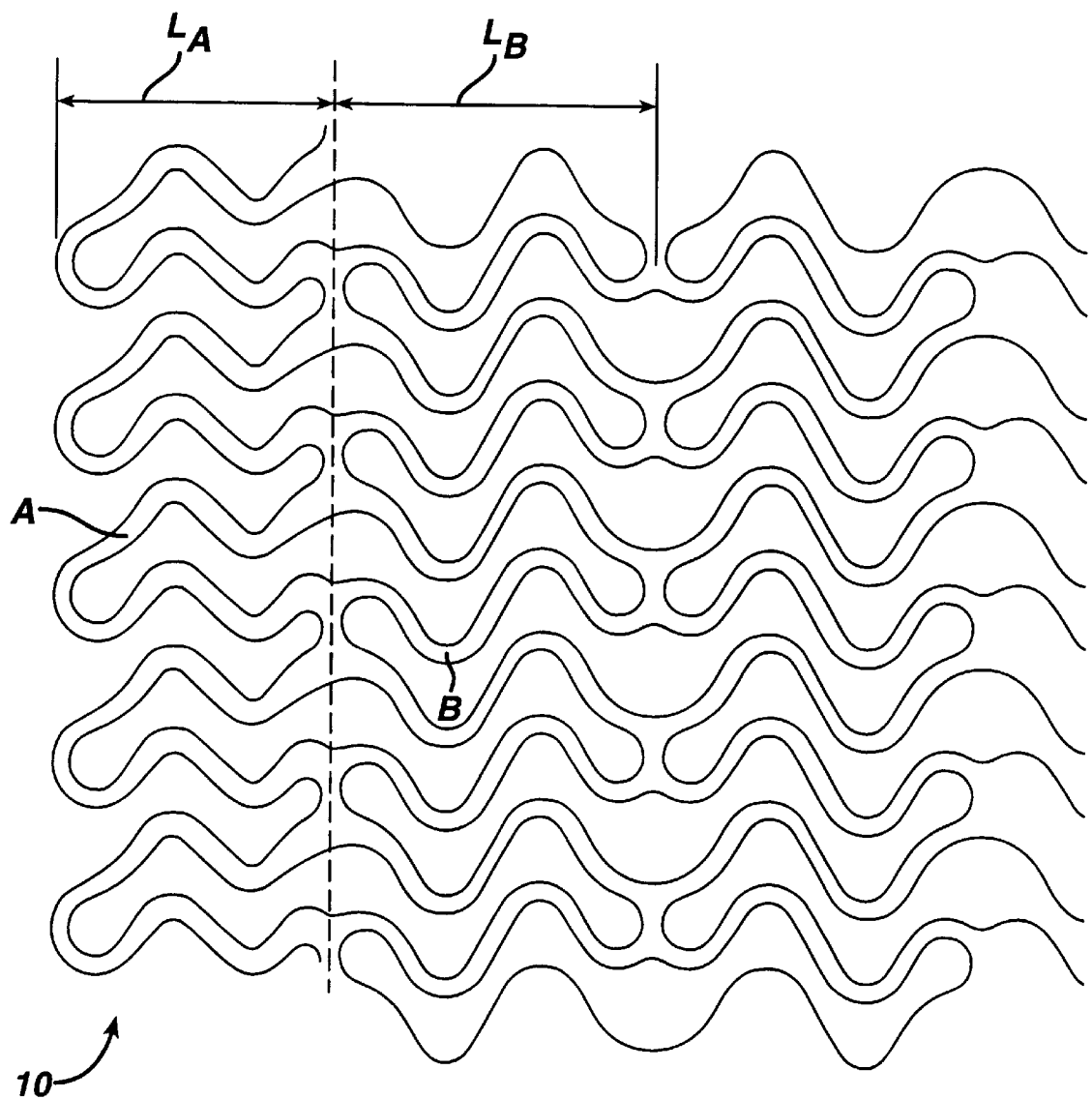
FIG. 7 shows a two dimensional layout of the stent. The ends are modified such that the length ($L_A$) is about 20% shorter than length ($L_B$) and the width of the band A is greater than the width of band B.

In contrast, the novel design of a preferred embodiment is shown in FIGS. 1(c) and 1(d) and FIG. 7. There, the bands (3) are axially flexible and are arranged along the longitudinal axis, avoids such an effect when the stent 10 is bent, so the bent bands (4) do not protrude from the profile of the curve of the stent 10. Further, any flaring at the ends of the stent 10 that might occur with a stent 10 having a uniform structure is substantially eliminated by introducing a modification at the ends of the stent 10. This modification comprises decreasing the spatial frequency and increasing the width of the corresponding bands in a circumferential direction ($L_A$ and A) compared to that of the intermediate section. ($L_B$ and B).

In an embodiment of the invention, the spatial frequency $L_A$ may be decreased 0–50% with respect to $L_B$, and the width A may be increased in the range of 0–150% with respect to B. Other modifications at the ends of the stent 10 may include increasing the thickness of the wall of the stent 10 and selective electropolishing. These modifications protect the artery and any plaque from abrasion that may be caused by the stent 10 ends during insertion of the stent 10. The modification also may provide increased radio-opacity at the ends of the stent 10. Hence it may be possible to more accurately locate the stent 10 once it is in place in the body.

Figure 2:
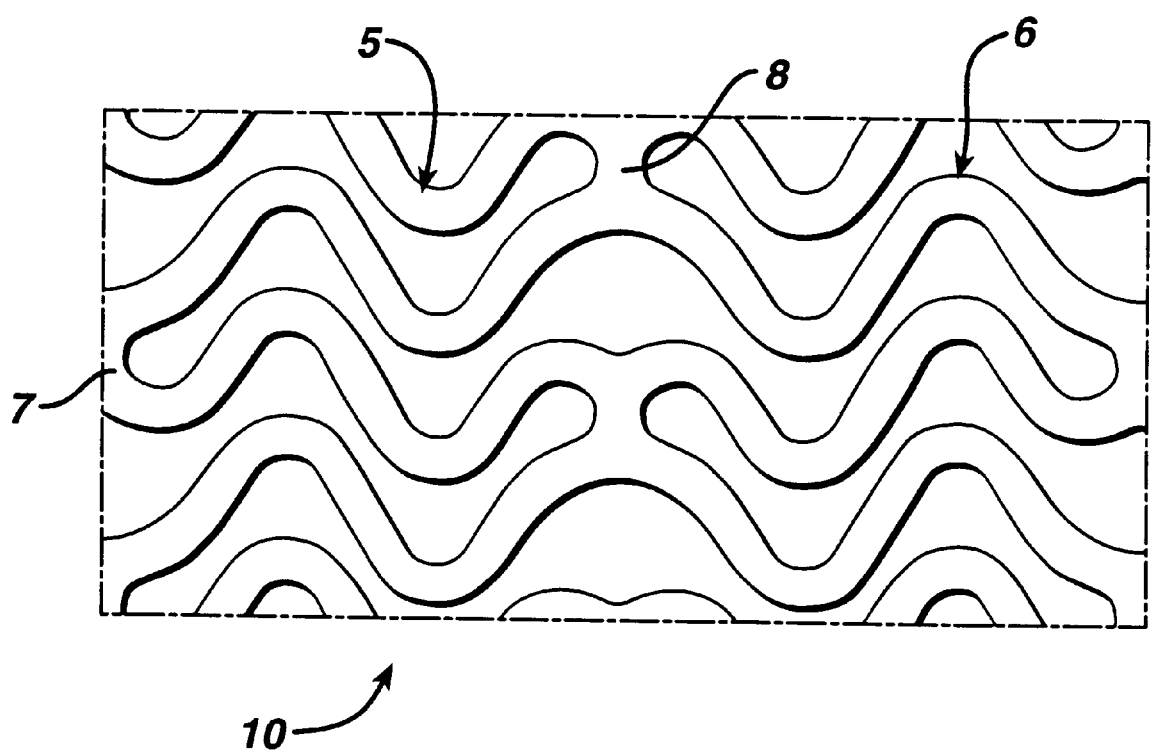
Figure 6:
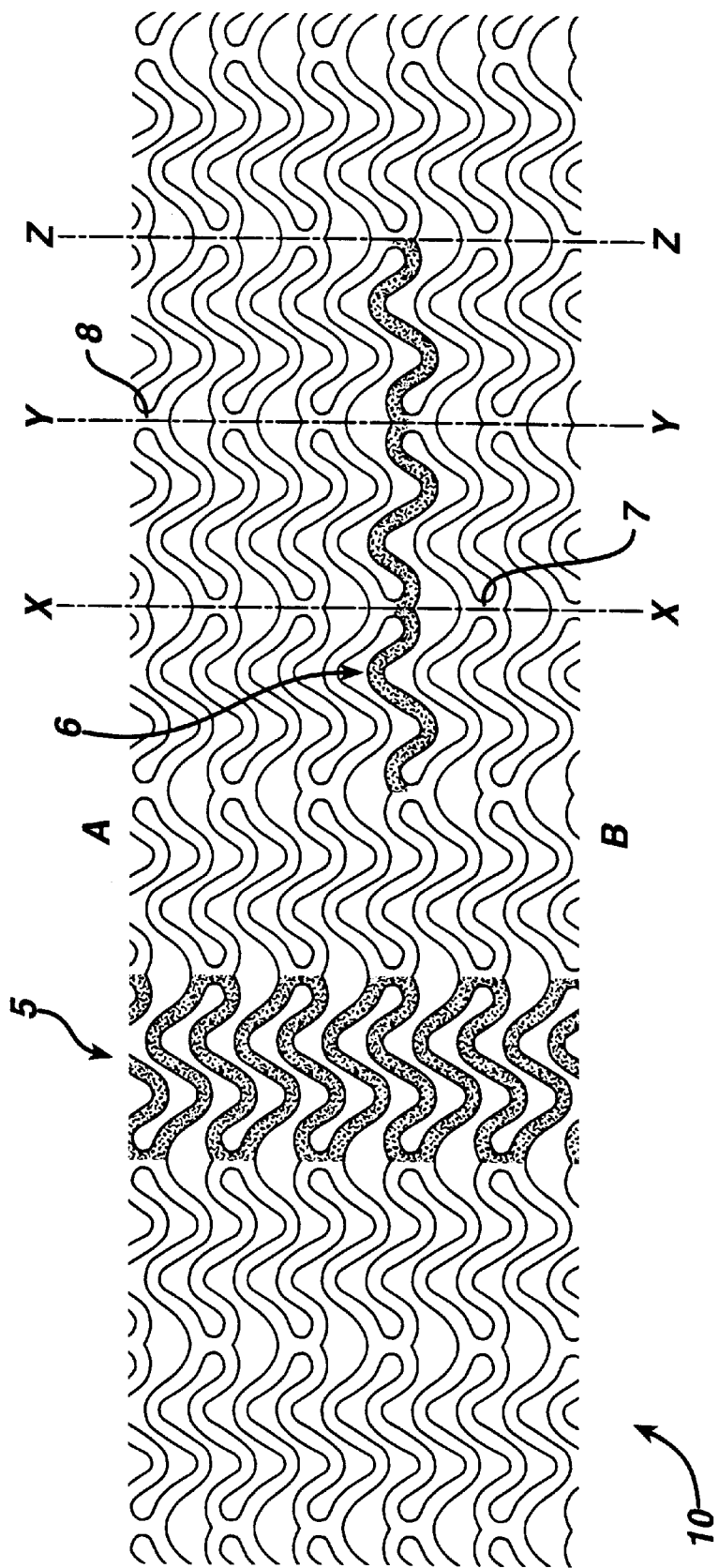
FIG. 6 shows a two-dimensional layout of the stent of FIG. 4 to form a cylinder such that edge "A" meets edge "B", and illustrating the spring-like action provided in circumferential and longitudinal directions.

The embodiment as shown in FIGS. 2 and 6 has the unique advantage of possessing effective "springs" in both circumferential and longitudinal directions shown as items (5) and (6) respectively. These springs provide the stent 10 with the flexibility necessary both to navigate vessels in the body with reduced friction and to expand at the selected site in a manner that provides the final necessary expanded dimensions without undue force while retaining structural resilience of the expanded structure.

Figure 4:
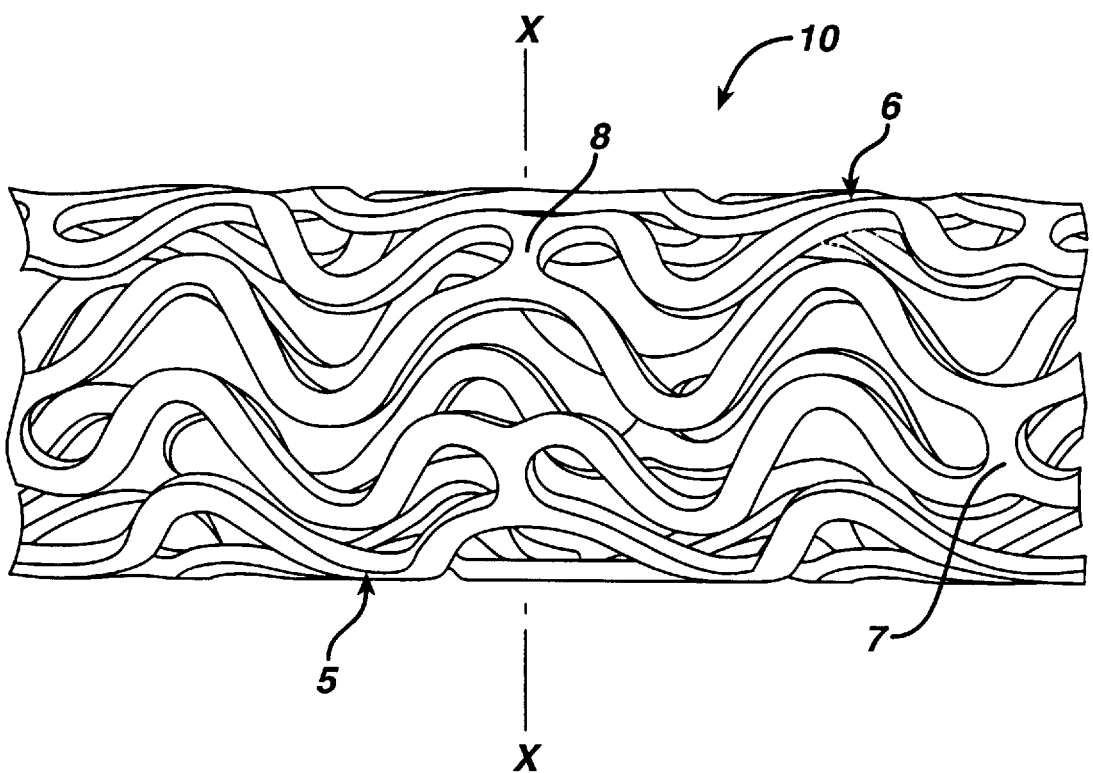
FIG. 4 is a view along the length of a piece of cylindrical stent (ends not shown) prior to expansion showing the exterior surface of the cylinder of the stent and the characteristic banding pattern.
Figure 5:
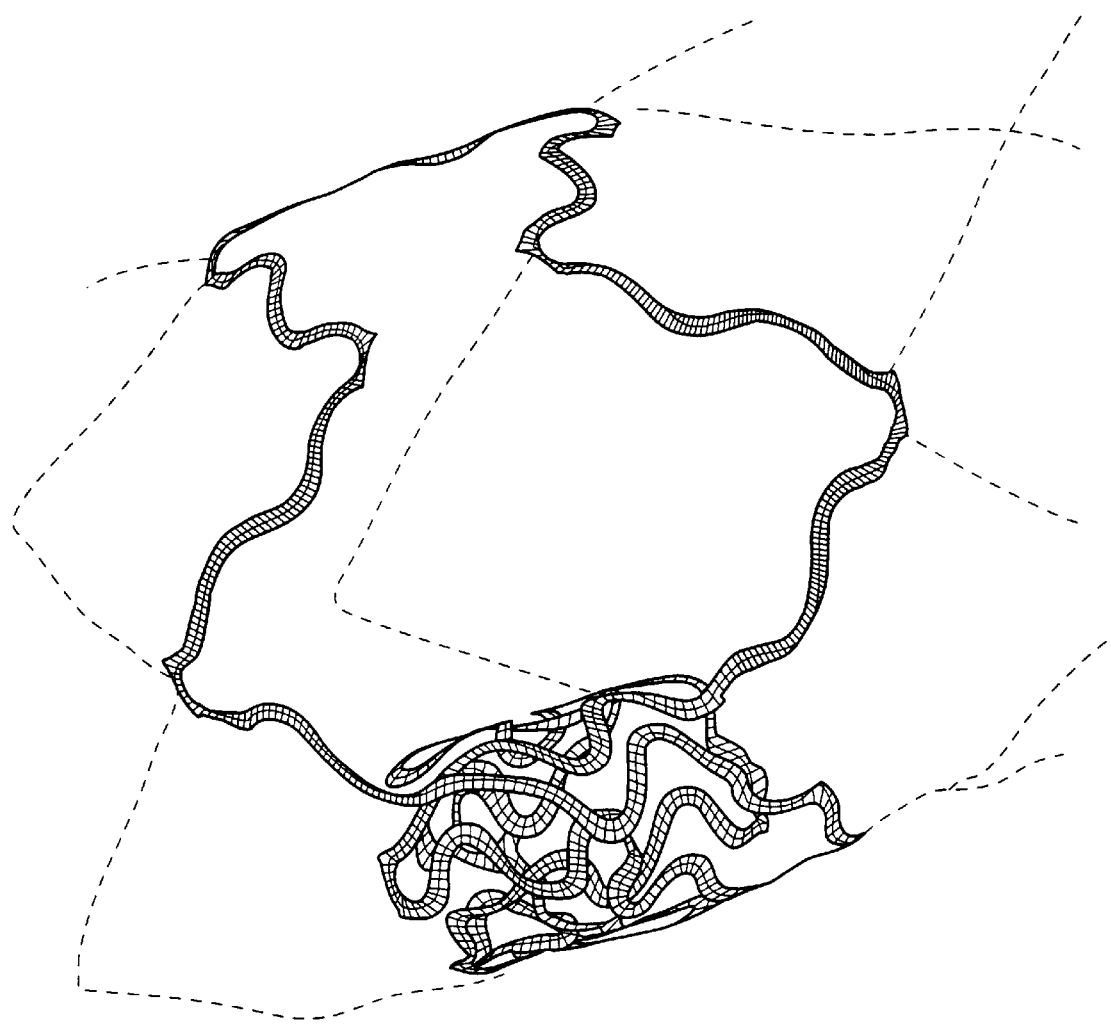
FIG. 5 is an isometric view of a deflection plot where the stent of FIG. 2 is expanded to a larger diameter of 5 mm.

As shown in both FIGS. 2, 4 and 6, each longitudinal band undulates through approximately two cycles before there is formed a circumferential link to an adjacent band. Prior to expansion, each waveform W associated with each of the bands will have approximately the same fundamental spatial frequency. The bands are so disposed that the wave W associated with them are spatially aligned, so as to be generally in phase with one another as shown in FIG. 6.

The aligned bands on the longitudinal axis are connected at a plurality of periodic locations, by a short circumferential link to an adjacent band. Consider a first common axial position such as shown by the line X—X in FIGS. 4 and 6. Here an adjacent pair of bands is joined by circumferential link 7. Similarly other pairs of bands are also linked at this common axial position. At a second common axial position, shown in FIG. 6 by the line Y—Y, an adjacent pair of bands is joined by circumferential link 8. However, any given pair of bands that is linked at X—X is not linked at Y—Y and vice-versa. The X—X pattern of linkages repeats at the common axial position Z—Z. In general, there are thus two groups of common axial positions. In each of the axial positions of any one group are links between the same pairs of adjacent bands, and the groups alternate along the longitudinal axis of the embodiment. In this way, circumferential spring 5 and the longitudinal spring 6 are provided.

A feature of the expansion event is that the pattern of open space in the stent 10 of the embodiment of FIG. 2 before expansion is different from the pattern of the stent 10 after expansion. In particular, in a preferred embodiment, the pattern of open space on the stent 10 before expansion is serpentine, whereas after expansion, the pattern approaches a diamond shape (3a, 3b). In embodiments of the invention, expansion may be achieved using pressure from an expanding balloon or by other mechanical means.

Figure 3A:
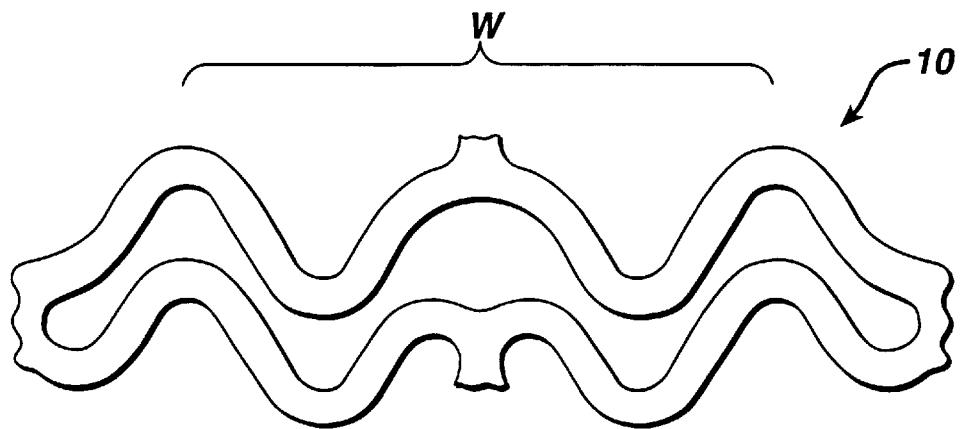
Figure 3B:
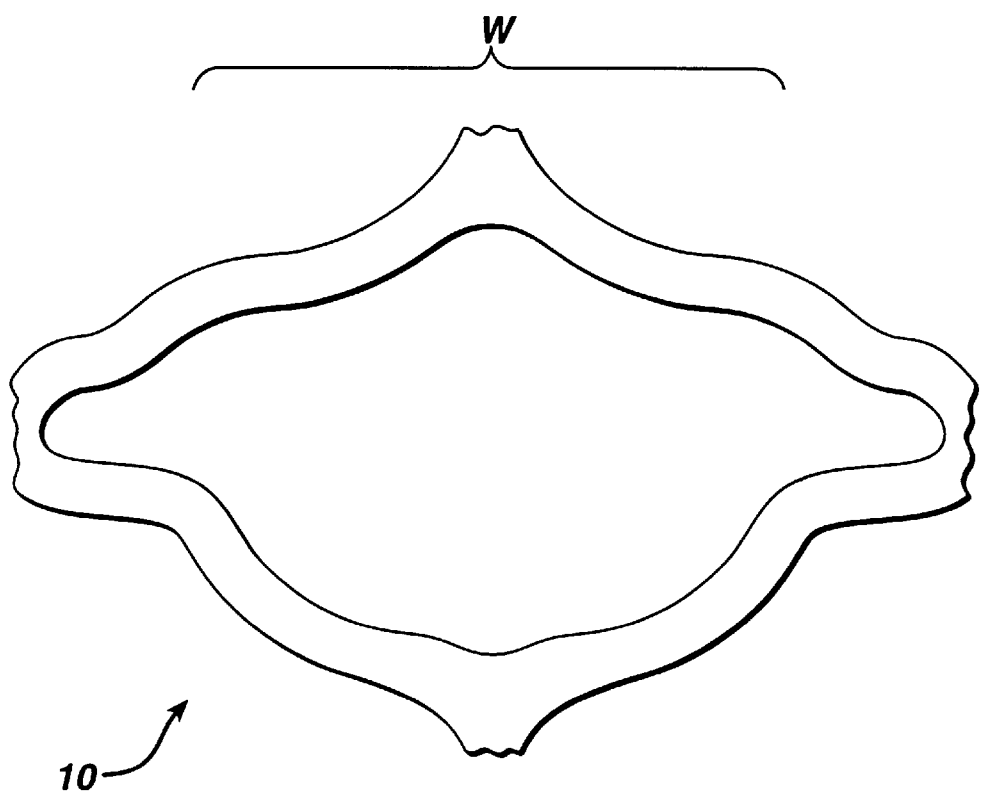

In the course of expansion, as shown in FIG. 3, the wave W shaped bands tend to become straighter. When the bands become straighter, they become stiffer and thereby withstand relatively high radial forces. FIG. 3 shows how radial expansion of the stent 10 causes the openings (or "fenestrations") to open up into a diamond shape with maximum stress being expended on the apices of the diamond along the longitudinal axis. When finite element analyses including strain studies were performed on the stent 10, it was found that maximum strain was experienced on the bands and links and was below the maximum identified as necessary to maintain structural integrity.

The optimization of strain of the stent 10 is achieved by creating as large a turn radius as possible in the wave W associated with each band in the non-expanded stent 10. This is accomplished while preserving a sufficient number of bands and links to preserve the structural integrity of the stent 10 after expansion. In an embodiment of the invention, the strain may be less than 0.57 inches/inch for 316L stainless steel. The expansion pressure may be 1.0–7.0 atmospheres. The number of bands and the spatial frequency of the wave W on the longitudinal axis also affect the number of circumferential links. The circumferential links contribute structural integrity during application of radial force used in expansion of the stent 10 and in the maintenance of the expanded form. It is to be noted that the current invention is not limited to a single set of parameters. Nonetheless, an example of a stent 10 of the invention having a longitudinal axis and providing axial flexibility as described above is shown in FIG. 6. This stent 10 has an expanded diameter of 4 mm and a length of 30 mm. For example, it may have about 8–12 rows, more particularly 10 rows and about 6–10 slots, more particularly 8 slots (a slot is shown in FIG. 6 as extending between X and Z). The stent may also have a wave W amplitude of about $1/4$–$1/10$ of a slot length, more particularly $1/8$ of a slot length.

The stent 10 may be fabricated from many methods. For example, the stent 10 may be fabricated from a hollow or formed stainless steel tube that may be cut out using lasers, electric discharge milling (EDM), chemical etching or other means. The stent 10 is inserted into the body and placed at the desired site in an unexpanded form. In a preferred embodiment, expansion of the stent 10 is effected in a blood vessel by means of a balloon catheter, where the final diameter of the stent 10 is a function of the diameter of the balloon catheter used.

In contrast to stents of the prior art, the stent 10 of the invention can be made at any desired length, most preferably at a nominal 30 mm length that can be extended or diminished by increments, for example 1.9 mm increments.

It will be appreciated that a stent 10 in accordance with the present invention may be embodied in a shape memory material, including, for example, an appropriate alloy of nickel and titanium; or stainless steel. In this embodiment after the stent 10 has been formed, it may be compressed so as to occupy a space sufficiently small as to permit its insertion in a blood vessel or other tissue by insertion means, wherein the insertion means include a suitable catheter, or flexible rod. On emerging from the catheter, the stent 10 may be configured to expand into the desired configuration where the expansion is automatic or triggered by a change in pressure, temperature or electrical stimulation.

An embodiment of the improved stent 10 has utility not only within blood vessels as described above but also in any tubular system of the body such as the bile ducts, the urinary system, the digestive tube, and the tubes of the reproductive system in both men and women.

Figure 8:
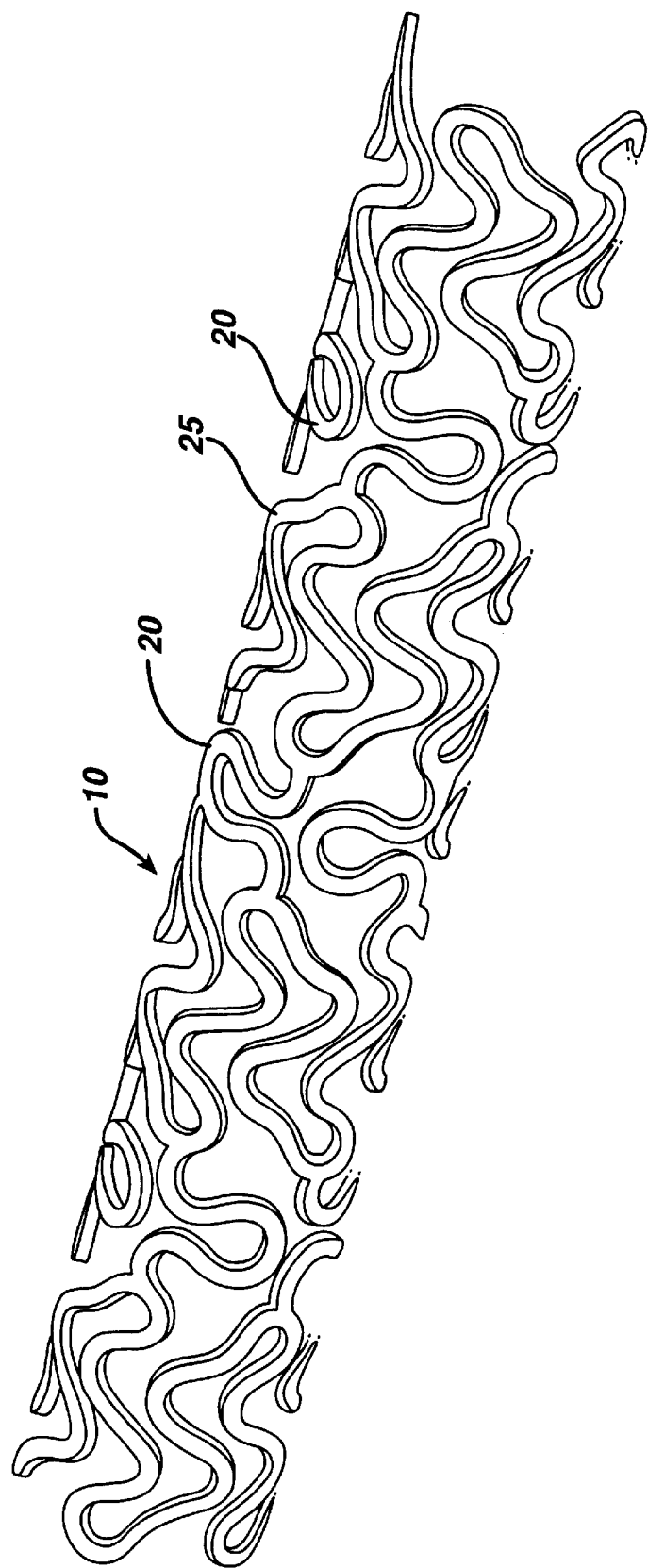
FIG. 8 shows a perspective view of a stent containing flexible connectors as described in the present invention.

In yet a further embodiment as illustrated in FIG. 8, there is described a stent 10 as presently disclosed comprising multiplicity of curvilinear segments 20. These curvilinear segments 20 are connected to each other via a generally perpendicular connector 25. The generally perpendicular connector 25 lies substantially in the plane perpendicular to the longitudinal axis of the stent 10. Each of the stent 10 segments as described herein is connected to an adjacent stent 10 segment. This is done using a series of flexible connectors. Importantly, the connectors themselves can be made narrower at their midpoints. This enhances the possibility of flexure at that point. Of course, it is to be realized that alternate designs of the connector to insure flexibility are possible, and contemplated by this invention.

In essence, therefore, the stent 10 as described in FIG. 8 is a stent 10 of considerable flexibility when compared to more rigid rectilinear stents. Nonetheless, the stent 10 of the present invention does not depart from the basic concepts set forth herein, in that it discloses a continuously curvilinear strut. This curvilinear strut is connected to other curvilinear struts via a series of "second" (more flexible) connectors, as described above.

In any regard, it can be seen that the stent 10 of the present invention incorporates various new and useful members. One of them is the flexible connector in conjunction with a generally curvilinear stent. Another is the use of the generally larger struts at the ends of the stent 10 in order to provide for continued support at the stent 10 ends. A final aspect is the use of flexible connectors amongst stent 10 segments to provide for greater flexibility.

In all regards, however, it is to be seen that the present invention is to be determined from the attached claims and their equivalents.

Figure 9:
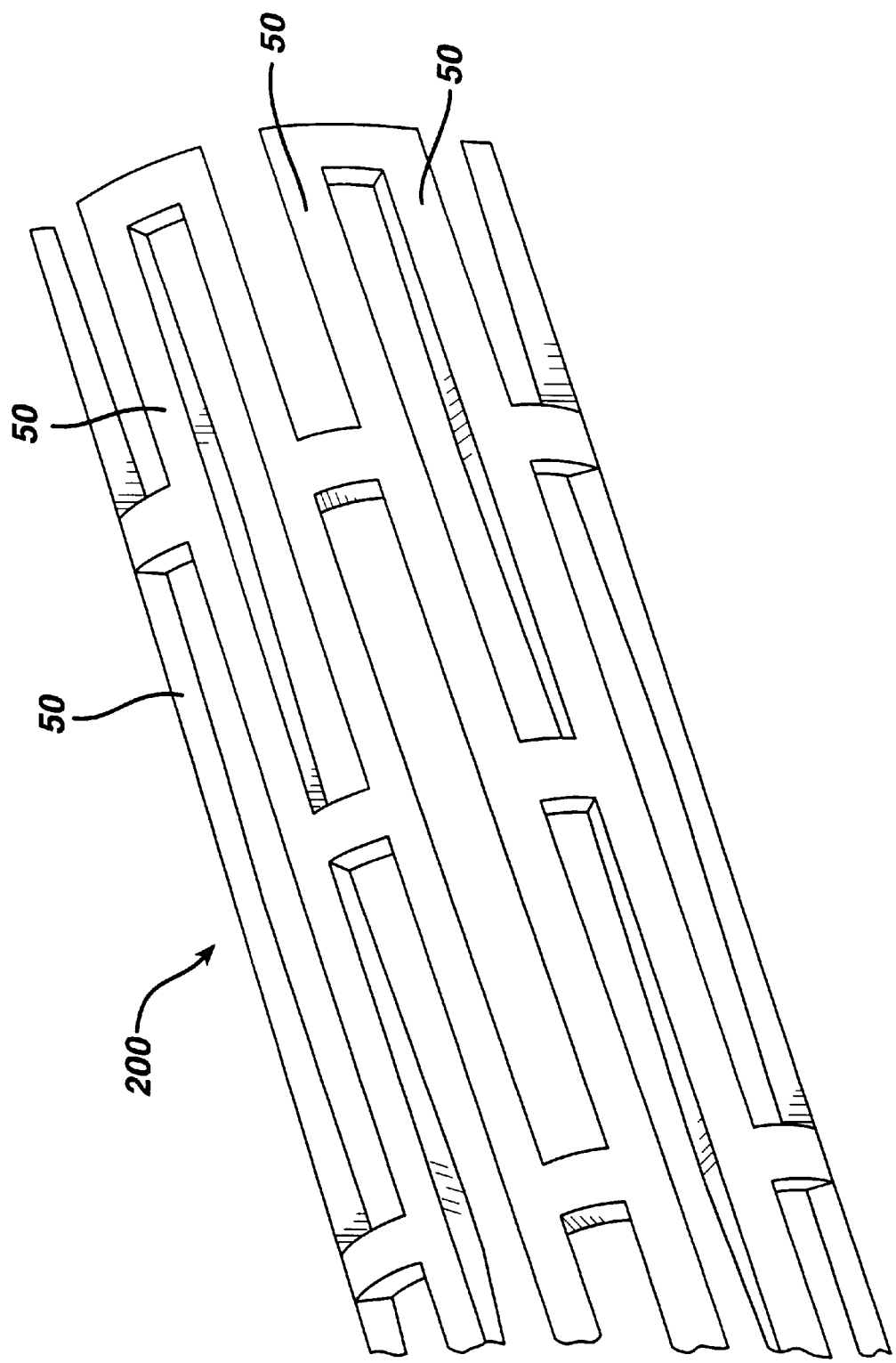
FIG. 9 is a perspective view of the stent of the present invention.
Figure 10A:
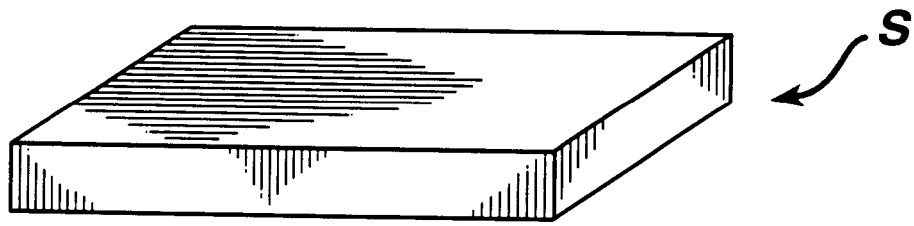
FIGS. 10a and 10b are plan views of a metal sheet which is formed into a stent of the present invention.
Figure 10B:
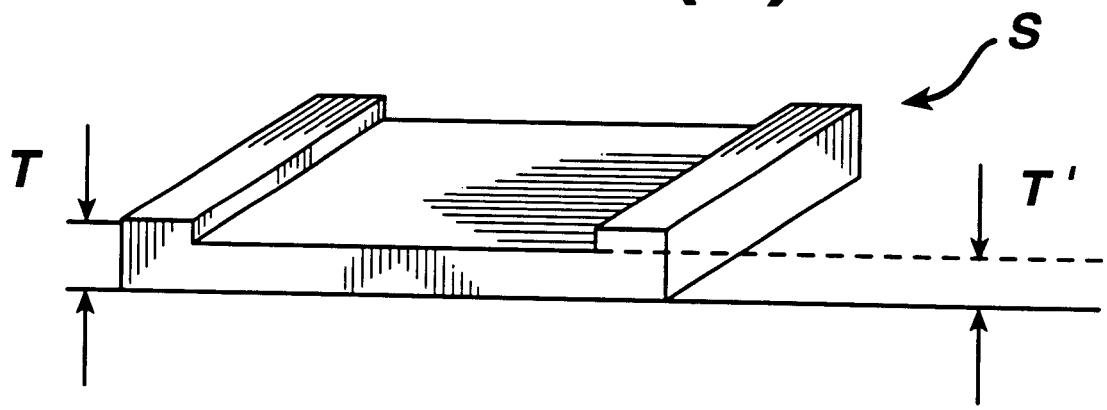
Figure 11:
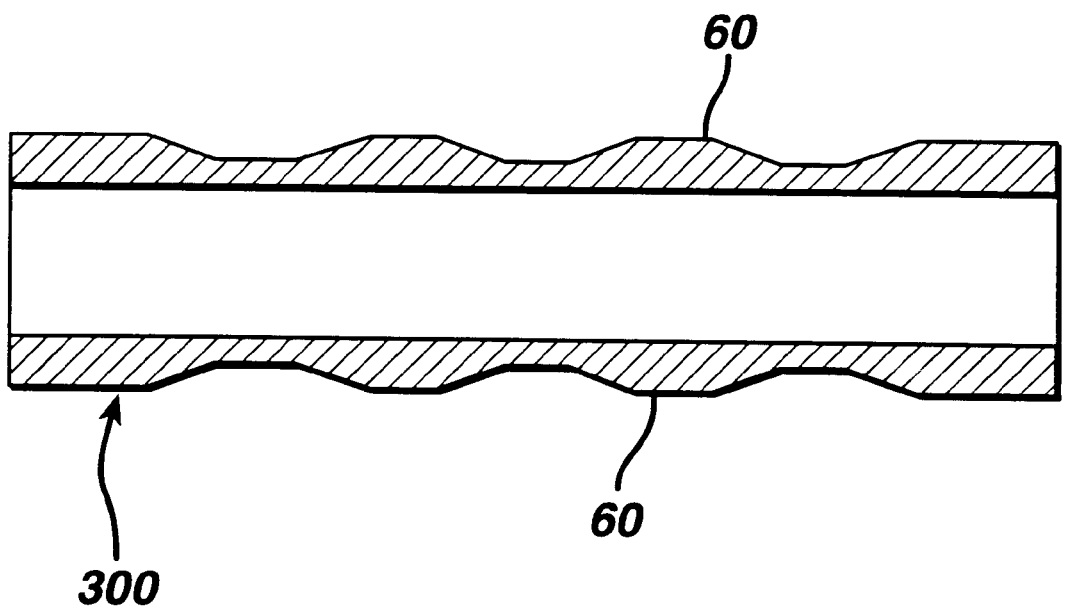
FIGS. 11 and 12 are still other alternate embodiments of the present invention.

As seen in FIGS. 9–11, there is disclosed a novel method for manufacturing a stent which will have variable wall thicknesses. For instance, the stents 200, 300 of FIG. 9 and 11 each contain struts 50, 60. These struts 50,60 are, in typical stents, generally of uniform thickness. What may be desirable is to vary the thickness of the struts 50,60 so as to enhance flexibility of the stent.

As seen in FIGS. 10a and 10b, the stent of the present invention initially starts out as a sheet S of metal. Then, the metal sheet S is rolled in the central region appearing between the two dotted lines to the specified wall thickness for the middle region of the stent. The rolling process produces a "texture" surface finish in the interior middle section of a stent. As seen in FIG. 10b, the stent sheet now has two wall thicknesses T, T'. One thickness T is contained at the proximal end of the stent. One thickness T is contained at the distal end of the stent. These typically kept the same. However, as can be seen better in FIG. 10b, the thickness T' in the middle of the stent is now narrower. It is perceived that this particular stent, when finally formed, will be more flexible in its middle sections, and more rigid in its distal and proximal ends. This may be desirable, for instance, where the stent is necessary to be "anchored" in the coronary artery.

Of course, this present stent size presents particular advantage. The rolling process produces a textured surface in the interior middle section of the stent. This textured surface will adhere more readily to the walls of the artery. Because the stent is thereafter rolled, no electro-polishing is involved in the fabrication of the stent, saving costs to manufacture.

As seen in FIGS. 9 and 11, the variable thickness of the stent can be made in a variety of locations. For instance in FIG. 9, the stent 200 has thicker ends than the middle section of the stent. But in FIG. 11, the stent 300 has thinner bridges than the serpentine pattern contained in the stent.

In addition to rolling it is clearly conceivable that the present invention can be accomplished by other metal forming methods. For instance, the center of the stent can be stamped and the stent ends welded to one another. In addition, the stent can be electropolished to reduce the thickness of the center of the stent. Or, the stent is laser-etched in both the thickness and the width of the struts. What is important however, is the ability of the stent to be made more flexible.

EXAMPLE 1

It may be desirable to describe a method for manufacturing the stent that is disclosed in FIGS. 9–11. This is done using a photochemical machine process. The stent would be photochemically machined from sheet material, 316L stainless steel in accordance with ASTM F 139. Tolerances of the sheet are kept within ±5% of the sheet thickness. For a typical stent with a finished wall of 0.003 inch, this would translate into ±0.00015 inch. Surface finish is maintained as specified in ASTM A 480, No. 8. (This is defined as a "mirror" finish, and is at least as good currently manufactured stents.) Tensile strength will be in accordance with the annealed temper defined in Table 3 of ASTM F 139. This creates an ultimate tensile strength of at least 71,000 psi, a yield strength of at least 27,500 psi, and a percentage elongation of 2 inch –40% min. Tolerances on the photochemically machined stent are kept within 10% of the material thickness. For a typical stent with a finished wall thickness of 0.003 inch this would translate to a strut/bridge tolerance of ±0.0003 inch.

Manufacturing takes place on a reel to reel machine. This would mean that the parts would be made from a single mask with identical dimensions on successive parts. The concept requires that the two sheet ends E, E', which are to be folded onto each other, are etched in such a way as to produce a joint with both tensile and shear components.

The process described above helps the performance of stents in three ways:

1. The strength of the joint (at the brazing point) would be greatly enhanced.

2. The "notch" in the struts (as seen in FIG. 9, for instance, and identified as N) would act as an alignment tool for lining up the ends to be brazed.

3. The increased surface area of the joint would insure that the joint, if brazed using a radiopaque alloy, would be visible with a fluoroscope.

With regard to roll forming the tube to make the stent, the annealed tempering of the material as described herein easily converts to being formed into a tube. Automated equipment capturing both the inner and outer diameters of the tube will be able to repeatedly form the tube (and therefore, the stent) to the appropriate configuration.

The brazing of the joint will be accomplished as follows. An alloy currently perceived to be useful is one consisting of 82% gold (Au) and 18% nickel (Ni). The alloy is controlled by Aerospace Material Specification (AMS) 4787. (It is known that the alloy is biocompatible.) The brazing cycle would involve temperatures currently being used to anneal under MIL-STD-889, Military Standard, Dissimilar Metals; this allows that under desired conditions, the Au—Ni braze alloy will not create a galvanic couple with the 316L stainless steel. The quality controls governing the brazed joint are in accordance with MIL-B-7883. One of the other advantages of the gold brazing alloy is the creation of a "radio-opaque" marker on the stent during the joining operation. This marker provides an easier to see stent under fluoroscopy.

Figure 12:
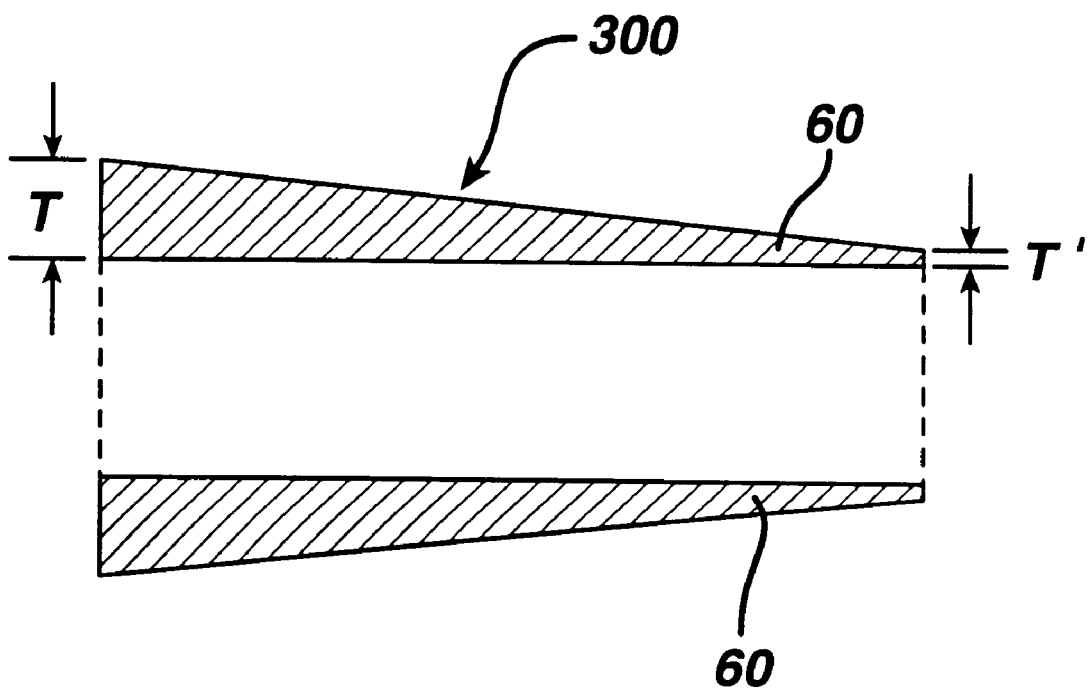

Finally, the stent of the invention may be etched so as to have tapered walls. The typical walls are seen in cross section in FIG. 12. This tapered wall allows the stent to be more flexible at one end as compared to the other.

Of course, alternate embodiments of the invention are possible without departing from the scope hereof. What the invention described herein is to be derived from the appended claims and their equivalents.

What is claimed is:

1. A stent comprising:
   a generally tubular device with a diameter and a length having a pattern of interconnected struts, said struts being cut from said tubular device, and said struts having a cross-sectional width and thickness; and
   said strut thickness being variable along the length of said stent; and
   wherein at least one of said struts with such a variable thickness comprises said strut having a relatively greater thickness, a relatively smaller thickness and a relatively intermediate thickness.

2. The stent of claim 1 used in combination with a balloon catheter.

3. The stent of claim 1 wherein said stent is self-expanding.

4. The stent as in claim 1 wherein said variable strut thickness is varied along the length of the strut so that said strut is thicker at its ends than in its middle.

5. The stent of claim 1 wherein said struts are configured so that there are portions of relative thickness and relative thinness along the length of the stent, and said portions of relative thickness are interspersed between said portions of relative thinness.

6. The stent of claim 1 wherein the stent has a portion of relative thickness at one of said ends, and a portion of relative thinness at a second of said ends.

7. A stent comprising:
  a balloon expandable mechanism formed from a series of interconnected struts, said struts having a cross-sectional width and thickness; and
  said strut thickness being variable along the length of said strut; and
  wherein at least one of said struts with such a variable thickness comprises said strut having a relatively greater thickness, a relatively smaller thickness and a relatively intermediate thickness.

8. The stent as in claim 7 wherein said variable strut thickness is varied along the length of the strut so that said strut is thicker at its ends than in its middle.

9. The stent of claim 7 wherein said struts are configured so that there are portions of relative thickness and relative thinness along the length of the stent, and said portions of relative thickness are interspersed between said portions of relative thinness.

10. The stent of claim 7 wherein the stent has a portion of relative thickness at one of said ends, and a portion of relative thinness at a second of said ends.

11. A stent comprising:
  a generally tubular device having a diameter and a length and a pattern of interconnected cells formed from a series of struts, said struts being cut into said tubular device and
  said struts having a cross-sectional width and thickness; and
  said strut thickness being variable along the length of said stent; and
  wherein at least one of said struts with such a variable thickness comprises said strut having a relatively greater thickness, a relatively smaller thickness and a relatively intermediate thickness.

12. The stent as in claim 11 wherein said variable strut thickness is varied along the length of the strut so that said strut is thicker at its ends than in its middle.

13. The stent of claim 11 wherein said struts are configured so that there are portions of relative thickness and relative thinness along the length of the stent, and said portions of relative thickness are interspersed between said portions of relative thinness.

14. The stent of claim 11 wherein the stent has a portion of relative thickness at one of said ends, and a portion of relative thinness at a second of said ends.

* * * * *